(12) United States Patent
Cheng

(10) Patent No.: US 7,279,010 B2
(45) Date of Patent: Oct. 9, 2007

(54) PROSTHETIC KNEE JOINT STRUCTURE

(76) Inventor: Yao-Teng Cheng, No. 6, Alley 22, Lane 49, Tung Feng Street, Shulin, Taipei Hsien (TW)

( * ) Notice: Subject to any disclaimer, the term of this patent is extended or adjusted under 35 U.S.C. 154(b) by 157 days.

(21) Appl. No.: 11/305,149

(22) Filed: Dec. 19, 2005

(65) Prior Publication Data

US 2006/0095141 A1 May 4, 2006

Related U.S. Application Data

(63) Continuation-in-part of application No. 10/625,660, filed on Jul. 24, 2003, now Pat. No. 7,044,983.

(30) Foreign Application Priority Data

Dec. 31, 2004 (TW) .............................. 093221322

(51) Int. Cl.
*A61F 2/64* (2006.01)
*A61F 2/68* (2006.01)

(52) U.S. Cl. ........................................... 623/46

(58) Field of Classification Search ............. 623/39–46
See application file for complete search history.

(56) References Cited

U.S. PATENT DOCUMENTS

| 5,904,721 | A | * | 5/1999 | Henry et al. | 623/26 |
| 6,117,177 | A | * | 9/2000 | Chen et al. | 623/44 |
| 7,044,983 | B1 | * | 5/2006 | Cheng | 623/46 |
| 2002/0188355 | A1 | * | 12/2002 | Chen | 623/45 |

* cited by examiner

*Primary Examiner*—Bruce Snow
(74) *Attorney, Agent, or Firm*—Leong C. Lei

(57) ABSTRACT

A prosthetic knee joint structure is provided herein. The knee join mainly contains an upper member for connecting to a prosthetic thigh, a lower member for connecting to prosthetic shin and foot, a linking device for connecting the upper and lower members, a cushion element, and a resilient device. During walking, the resilient device prevents the shin from dangling and the knee joint from sudden bending and kneeling-down. The cushion element absorbs the shock when the prosthetic leg is walking on a flat ground or slope.

1 Claim, 7 Drawing Sheets

PROSTHETIC KNEE JOINT STRUCTURE

CROSS-REFERENCE TO RELATED APPLICATIONS

This is a continuation-in-part of U.S. application Ser. No. 10/625,660 filed Jul. 24, 2003 now U.S.Pat. No. 7,044,983.

BACKGROUND OF THE INVENTION (a) Technical Field of the Invention

The present invention generally relates to prosthetic legs, and more particularly to a knee joint for prosthetic legs which confines the bending angle within a range and absorbs the shocks during walking.

(b) Description of the Prior Art

The most important and complicated part of a prosthetic leg is the knee joint. The prosthetic knee joint not only should work like a real human joint, but also should make the user walk in a natural way.

Conventional prosthetic knee joints, as disclosed in R.O.C. Patent No. 549,074, utilize a plurality of joining elements to link a prosthetic thigh and prosthetic shin and foot. The prosthetic knee joint could imitate how a real human joint bends, and a cushion pad is configured on a lower joining element for absorbing the shock from the ground.

The drawbacks of these conventional prosthetic knee joints are as follows. The shock absorbing capability of the cushion pad is only available when the prosthetic thigh and shin are aligned in a straight line when the leg is landed on the ground. This is of no concern for a user walking on a flat ground. However, when the user is walking downhill, the prosthetic leg is bended with a small angle and the cushion pad is therefore unable to absorb the shock. In addition, the joining elements of the conventional prosthetic knee joint are unable to keep the bending of the prosthetic leg within a range. Therefore, when the user is walking on flat ground or on a slope, the shin would dangle from the knee joint when the prosthetic leg is lifted from the ground, causing the user to suddenly kneel down. Accordingly, there is a need for a better structured prosthetic knee joint that could imitate more naturally how real people walk.

SUMMARY OF THE INVENTION

Accordingly, a prosthetic knee joint is disclosed herein that could obviate the problem of shock absorbing when walking on a slope and the problem of sudden bending and kneeling down.

A major objective of the present invention is that, when the user is walking or standing, the bending of the prosthetic leg is confined within a range so that the shin wouldn't dangle, and the prosthetic leg is able to absorb shocks even when the prosthetic is bended within the specific range.

To achieve the foregoing objective, the prosthetic knee joint according to the present invention contains an upper member for connecting to a prosthetic thigh, a lower member for connecting to prosthetic shin and foot, a linking device for connecting the upper and lower members which mainly includes a joining element and connecting rods, a cushion element, and a resilient device mainly including a supporting element, a first cap element, a first helical spring, a first adjustment screw, a second cap element, a second helical spring, a second adjustment screw, and a stopping plate. The resilient device, by the force exerted from the helical springs, confines the bending of the prosthetic knee joint within a specific range. The cushion element, on the other hand, is able to absorb the shock as long as the prosthetic knee joint is bended within the specific range.

The foregoing object and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are of exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 1:
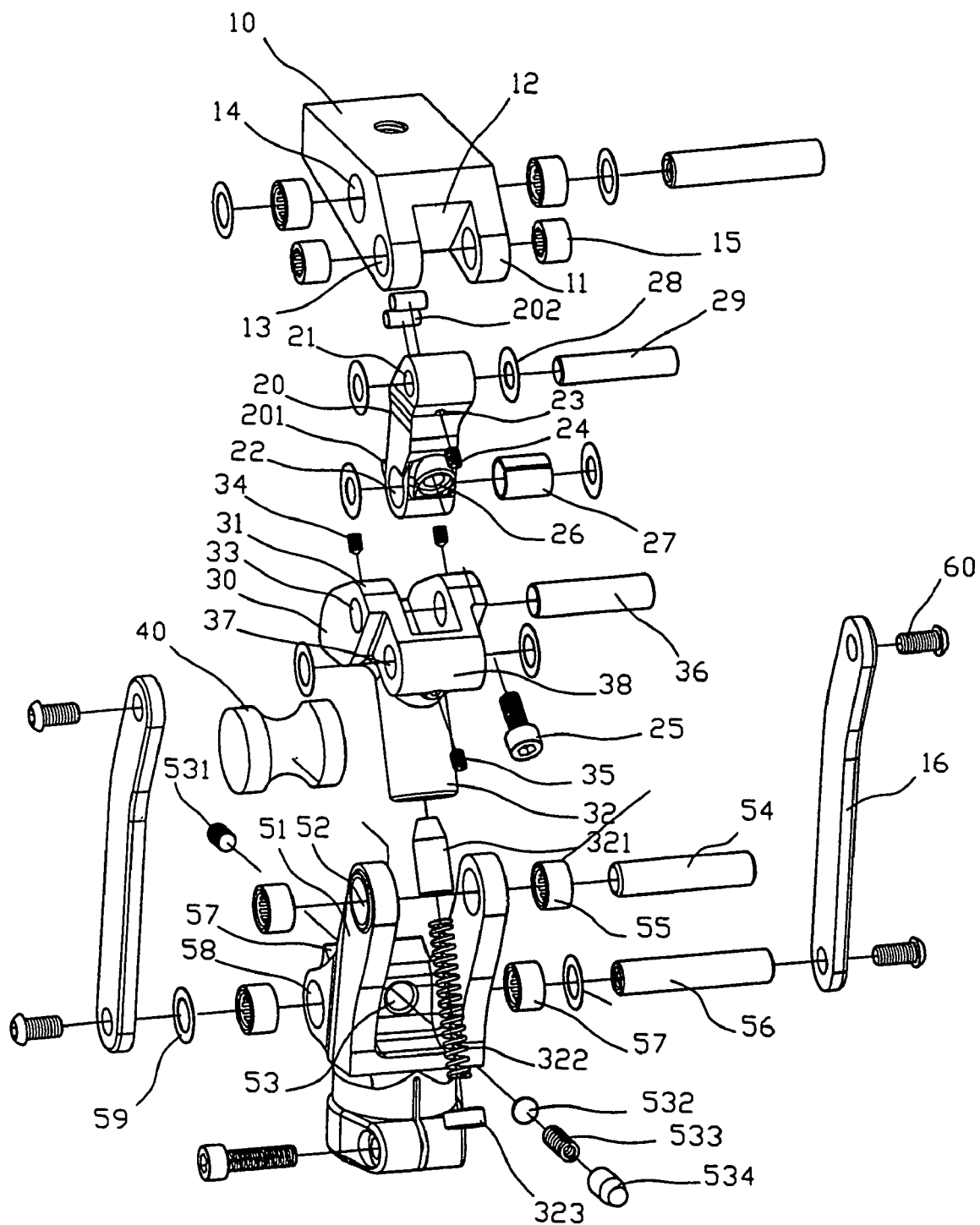
FIG. 1 is a perspective explosion view showing the various components of a knee joint according an embodiment of the present invention.

As illustrated in FIG. 1, an embodiment of the prosthetic knee joint according to the present invention contains an upper member 10 for connecting to a prosthetic thigh, a lower member 50 for connecting to prosthetic shin and foot, a lining device for connecting the upper and lower members 10 and 50 which mainly includes a joining element 20 and connecting rods 16, a cushion element 40, and a resilient device for shock absorption. The resilient device in turn mainly includes a supporting element 30, a first cap element 321, a first helical spring 322, a first adjustment screw 323, a second cap element 534, a second helical spring 533, a second adjustment screw 531, and a stopping plate 532. For ease of reference, locations closer to the upper member 10 are said to be higher or above those locations farther away from the upper member 10, hereinafter.

The upper member 10 has a solid body with a lateral through hole 14 in the middle of the body. The lateral through hole 14 is for screw-joint with the top ends of the connecting rods 16. The lower end of the upper member 10 is forked into two arms 11 with a hollow space 12 therebetween. The fork arms 11 have aligned lateral through holes 13, parallel to the body's through hole 14. The hollow space 12 is for accepting an upper portion of the joining element 20. At where the upper member 10 and the joining element 20 interface with each other, the upper member 10 and the joining element 20 are configured with matching slant surfaces. On the slant surface of the joining element 20, there are grooves (see FIG. 2) for the installation of cushiony blocks 202. In the upper portion of the joining element 20, there is a lateral through hole 21 which would be aligned with the through holes 13 of the fork arms 11 when the joining element 20 is positioned in the hollow space 12. Needle bearings 15 are installed in the through holes 13 of the fork arms 11. An axle 29 is threaded through the aligned through holes 13 and 21 and washers 28 which is inserted between the fork arms 11 and the joining element 20. On a front side of the joining element 20, there is a threaded hole 23 through which a positioning screw 24 could be screwed in to fixedly lock the axle 29.

In the lower portion of the joining element 20, there is a lateral through hole 22 parallel to the upper through hole 21. A bushing 27 is installed inside the through hole 22. In the upper portion of the supporting element 30, there are fork arms 31 surrounding a hollow space (not numbered) for accepting the lower portion of the joining element 20. The fork arms 31 have lateral through holes 33 which would be aligned with the through hole 22 when the joining element 20 is positioned between the fork arms 31. An axle 36 is threaded through the through holes 33 and 22 to join the joining element 20 and the supporting element 30 together. Positioning screws 34 are screwed into threaded holes (not shown) on the fork arms 33 to lock the axle 36. On the front side of the lower portion of the joining element 20, there is an adjustment screw hole 26 for the installation of an adjustment screw 25. The adjustment screw 25 is pressed against the supporting element 30 (see FIG. 2). The adjustment screw 25, along with the first cap element 321, confines the bending angle between the joining element 20 and the supporting element 30 within a specific range.

The back side of the supporting element 30 is curved so as to match the curved surface of the cushion element 40. The supporting element 30 has a protruding portion 38 in the front and beneath the fork arms 31. The protruding portion 38 has a lateral through hole 37. In the upper portion of the lower member 50, there are fork arms 51 surrounding a hollow space (not numbered) for accepting the lower portion of the supporting element 30. The fork arms 51 have lateral through holes 52 which would be aligned with the through hole 37 when the supporting element 30 is positioned between the fork arms 51. Needle bearings 55 are installed inside the through holes 52. An axle 54 is threaded through the aligned through holes 37 and 52 to join the supporting element 30 and the lower member 50 together. A positioning screw 35 is screwed into a threaded hole (not shown) on the protruding portion 38 to lock the axle 54. The supporting element 30 has a tubular portion 32 within which the first cap element 321 and the first helical spring 322 are locked by the first adjustment screw 323. The first adjustment screw 323 is also for adjusting the resilient force of the helical spring 322.

Figure 2:
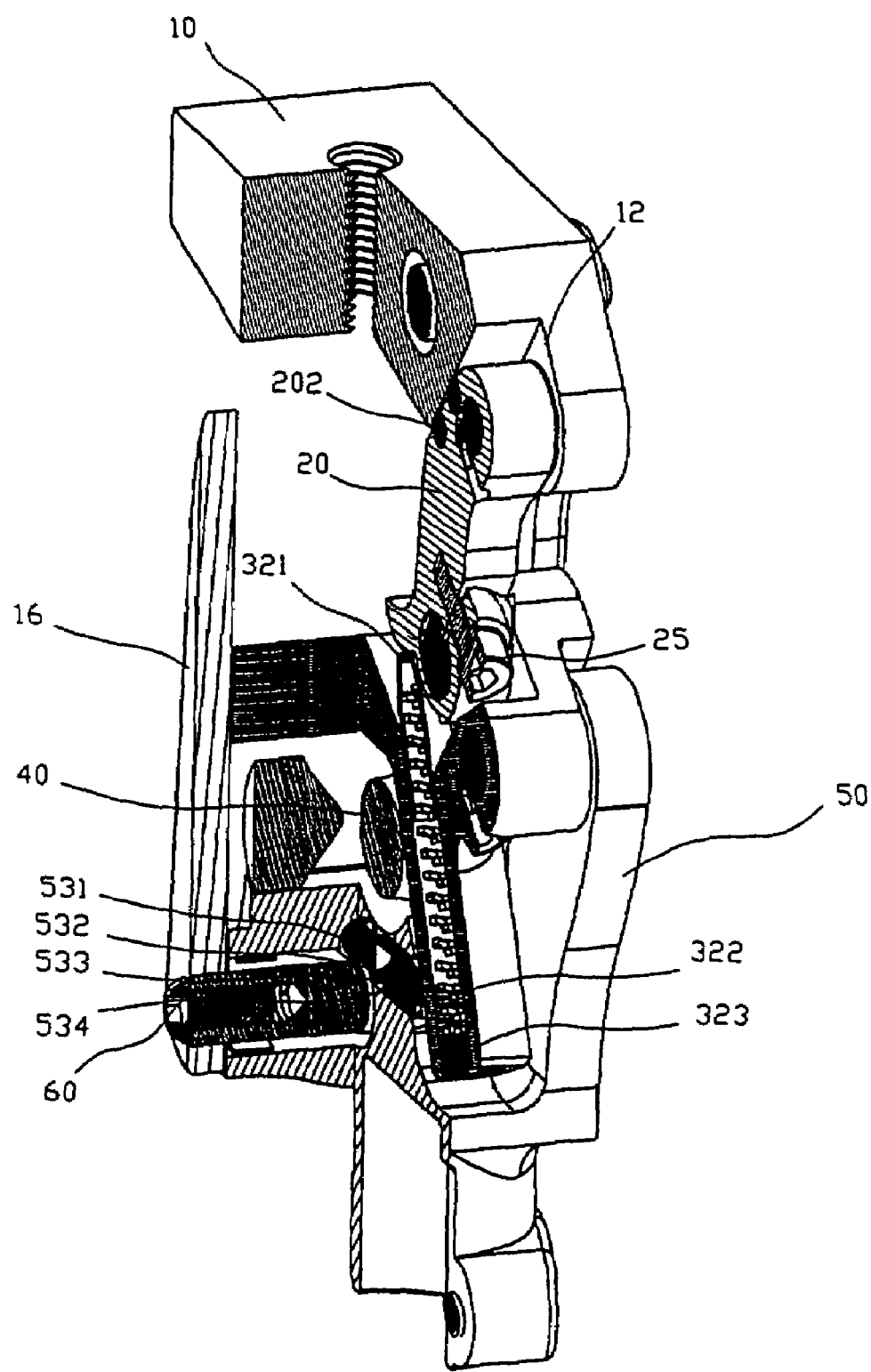
FIG. 2 is a partial sectional view showing the knee joint of FIG. 1.

At the back side of the lower member 50, there is a curved seat 57 for the placement of the cushion element 40. The lower member 50 has a lateral through hole 58 at the back side beneath the curved seat 57 and the fork arms 51. Needle bearings 57 are installed inside the through hole 58. An axle 56 is threaded through the washers 59 and through hole 58. The bottom ends of the connecting rods 16 are locked to the two end of the axle 56 by screws 60. Within the fork arms 51, the lower member 50 has a threaded hole 53 for the installation of the second cap element 534, the second helical spring 533, the stopping plate 532, and the second adjustment screw 531. The second cap element 534 is pressed against the tubular portion 32 of the supporting element 30. A partial sectional view of an assembled prosthetic knee joint according to the present embodiment is depicted in FIG. 2.

The assembly of the foregoing elements of the present embodiment is as follows. The joining element 20 is inserted into the hollow space 12, and the axle 29 is threaded through the aligned through holes 13 and 21. The axle 29 is then fixedly locked by the positioning screw 24. Similarly, the lower portion of the joining element 20 is placed between the fork arms 31 of the supporting element 30. The axle 36 is threaded through the aligned through holes 33 and 22. The axle 36 is then fixedly locked by the positioning screws 34. The first adjustment screw 323 is then engaged to control the helical spring 322 so that the first cap element 321 is pressed against a flange 201 in the back of the joining element 20 through the tubular portion 32 of the supporting element 30. The rotation of the joining element 20 is therefore confined by the first cap element 321 and the adjustment screw 25. The axle 54 is threaded through the aligned through holes 52 and 37. The axle 54 is then fixedly locked by the positioning screw 35. At this point, the upper member 10, the joining element 20, the supporting element 30, and the lower member 50 are basically joined together into a single structure. Then, at the two sides of the joined structure, the top ends of the connecting rods 16 are bolted to the through holes 14 and the bottom ends of the connecting rods 16 are bolted to the through holes 58 by a number of screws 60 respectively. The connecting rods 16 and the curved seat 57 of the lower member 50 jointly keep the cushion element 40 at its position. The second cap element 534, the second helical spring 533, the stopping plate 532, and the second adjustment screw 531 are then placed inside the through hole 53 so that the second cap element 534 is pressed against the tubular portion 32 of the supporting element 30. The joint function of the second cap element 534, the second helical spring 533, the stopping plate 532, and the second adjustment screw 531 are two folds: first, they could absorb the impact of the supporting element 30 when it is restored to an upright position; and, secondly, they could adjust the tilted angle of the supporting element 30, which in turn would affect the tilted angle of the upper member 10 via their interconnection mechanism.

When a user is standing, the supporting element 30 would be forced downward to press against the cushion element 40. The cushion element 40, made of a plastic material with superior elasticity, is therefore able to provide adequate buffering and make the user feel more comfortable. When the knee joint is in operation, the first and second helix springs 322 and 533, the first and second adjustment screws 323 and 531, the first and second cap elements 321 and 534, and the stopping plate 532 jointly help maintaining the joining element 20 in a steady state without causing sudden bending and kneeling-down. These elements also provide cushion and confine the supporting element 30 to swing only within a specific range.

The adjustment screw 531 controls the force exerted by the second helical spring 533 inside the supporting element 30. This would affect how easy the knee joint is bended and expanded.

FIGS. 3~6 shows the consecutive states of the knee joint of the present embodiment in an exemplary walking scenario. Within each diagram, a simplified line drawing showing the relative angles and positions of the various axles of the present embodiment is also provided.

Figures 3A, 3B:
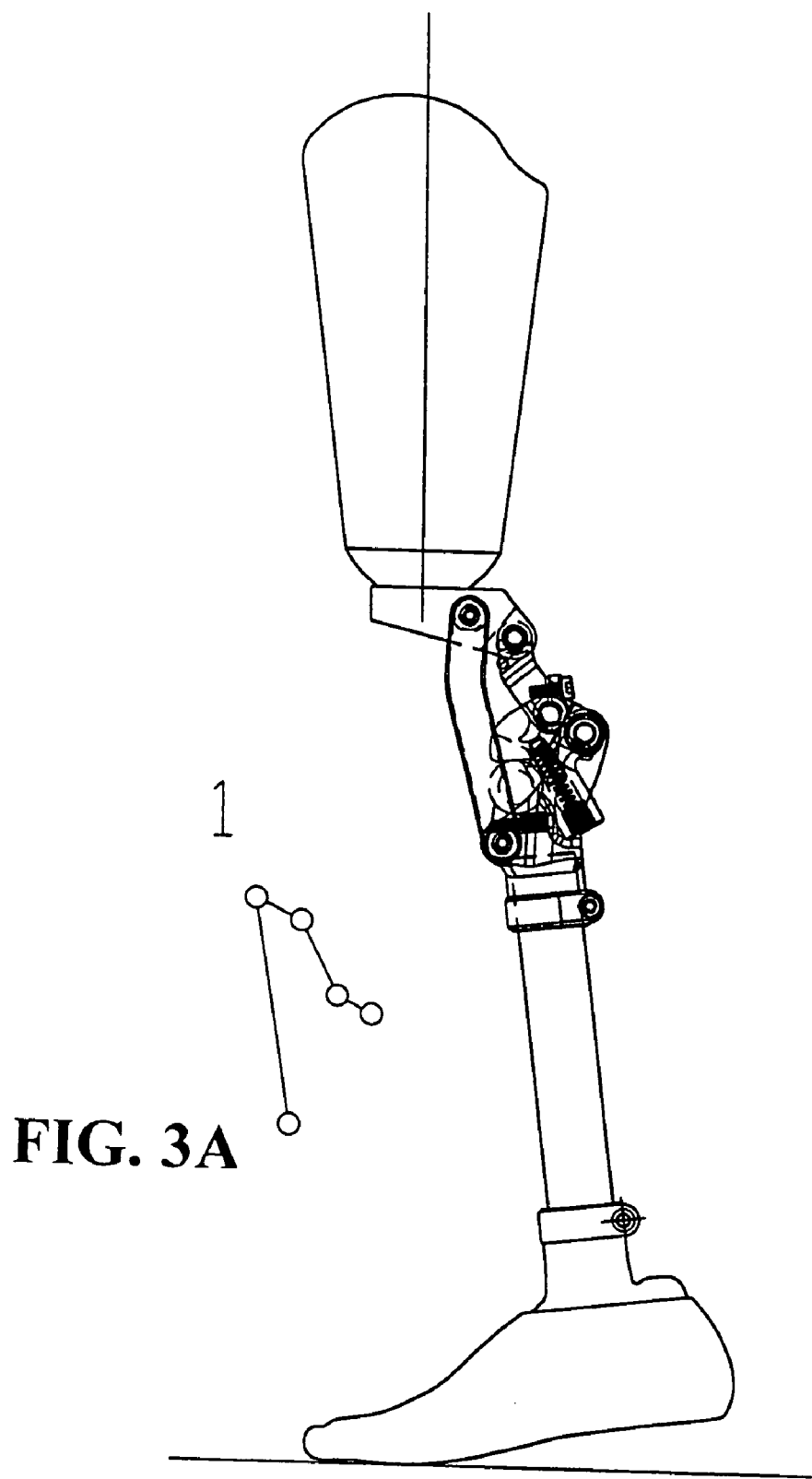
FIGS. 3~6 are schematic views showing the consecutive states of the knee joint of FIG. 1 in an exemplary walking scenario.
Figures 4A, 4B:
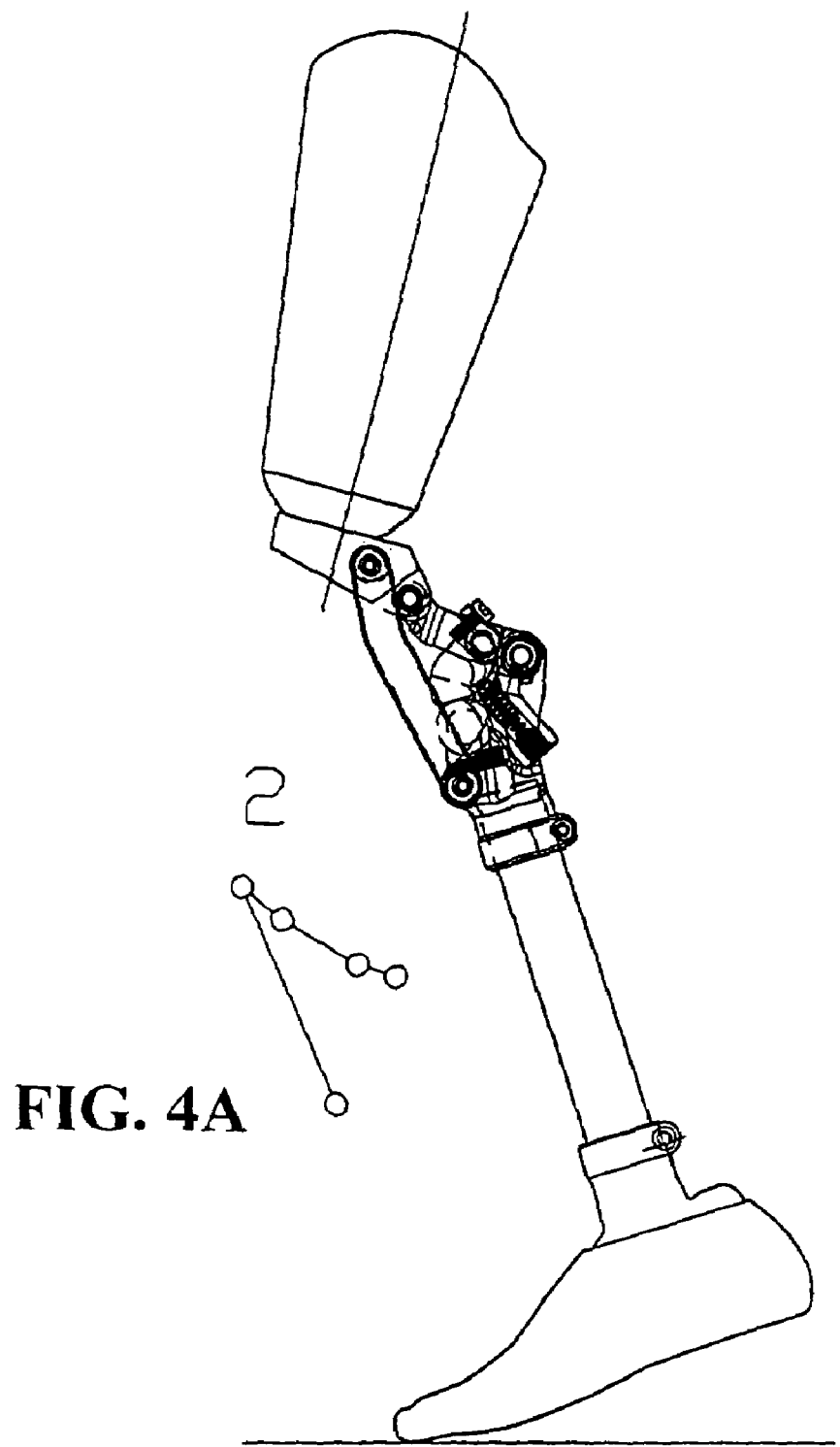
Figures 5A, 5B:
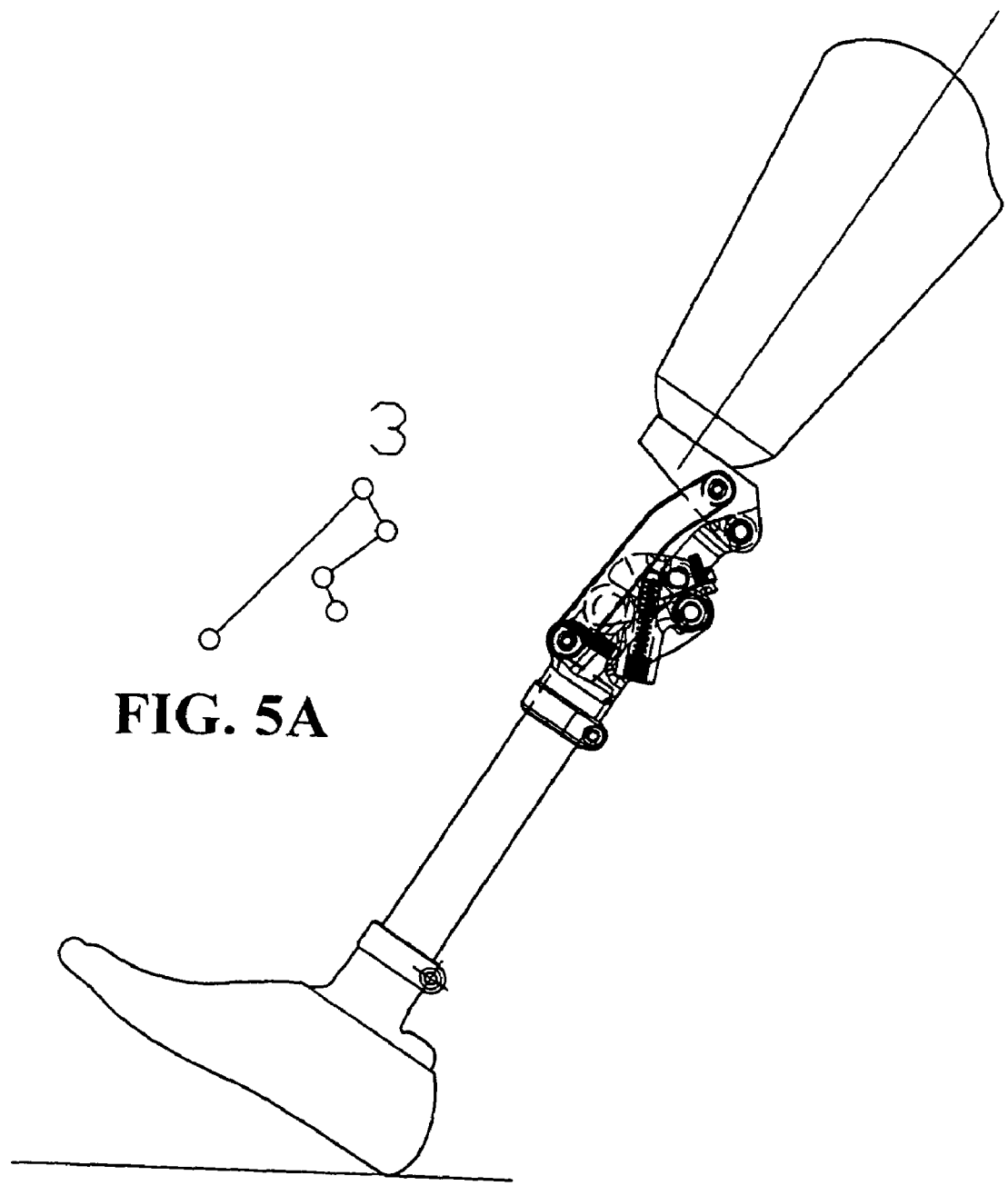
Figures 6A, 6B:
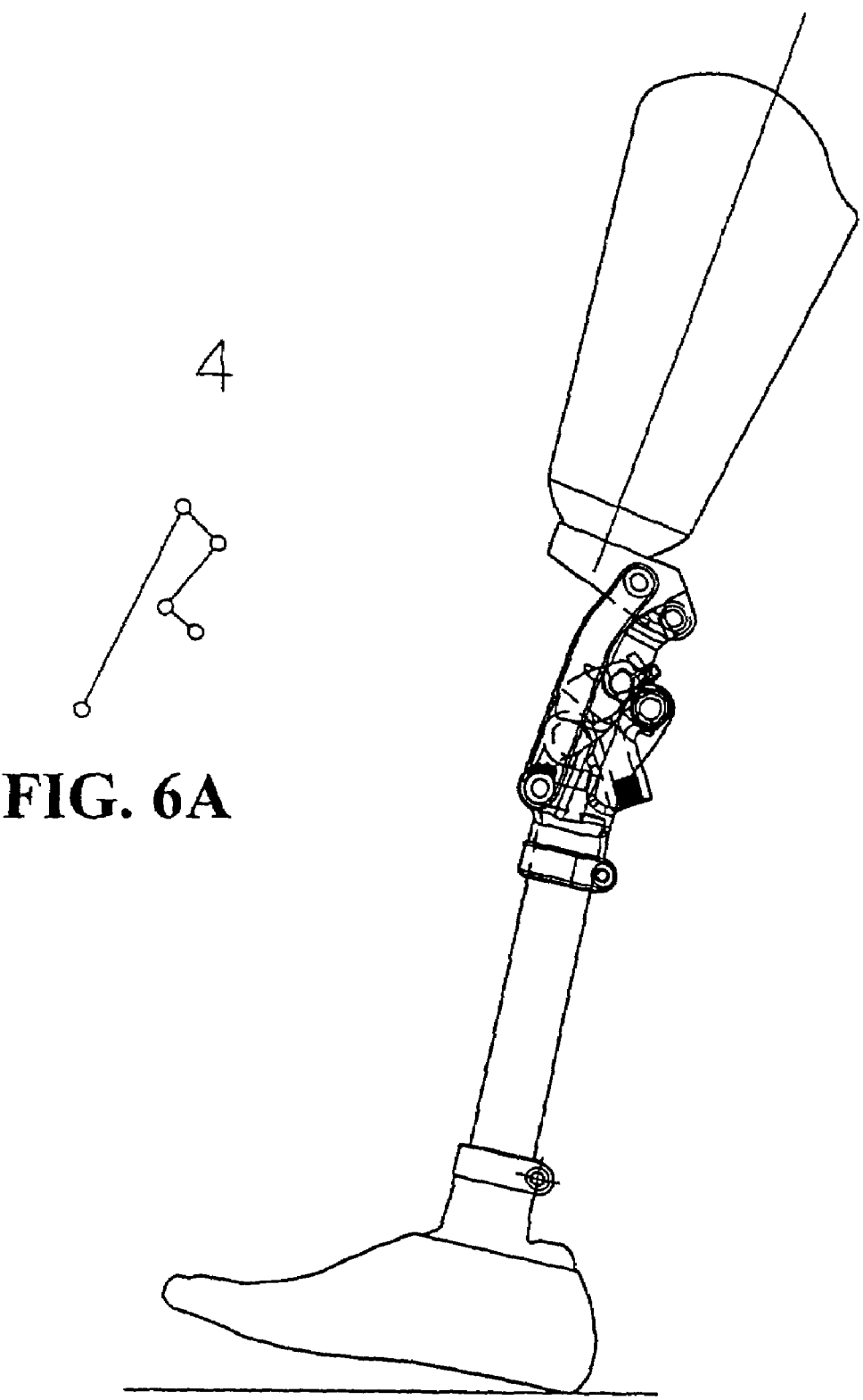

FIGS. 3A & 3B shows, in a first state, a prosthetic leg equipped with the present embodiment is about to be lifted from the ground in order to make a next step forward. FIGS. 4~5 shows two consecutive states of the leg, while FIGS. 6A-6B shows, in a fourth state, the present embodiment absorbs the shock as the leg's heel is firmly landed on the ground.

As shown, in the first state, the joining element 20 and the supporting element 30 are not under the pressure from walking and the axles 36 and 54 are located to the right of the axle 29. The helical springs 322 and 533 of the resilient device keep the joining element 20 at a stead state. Then, in the second state, the axles 36, 54, and 29 are aligned in a straight line, and the joining element 20 and the supporting element 30 are pressed to exhibit a bended state. In the third state, the axles 36 and 54 are moved to the left of the axle 29. The compressed springs of the resilient device exert force to support the joining element 20 and alter the angle between the joining element 20 and the supporting element 30 so that the shin of the prosthetic leg wouldn't dangle. At last, in the fourth state, the cushion element 40 absorbs the shock when the heel of prosthetic leg lands on the ground to ensure the comfort and safety of the user.

Figure 7:
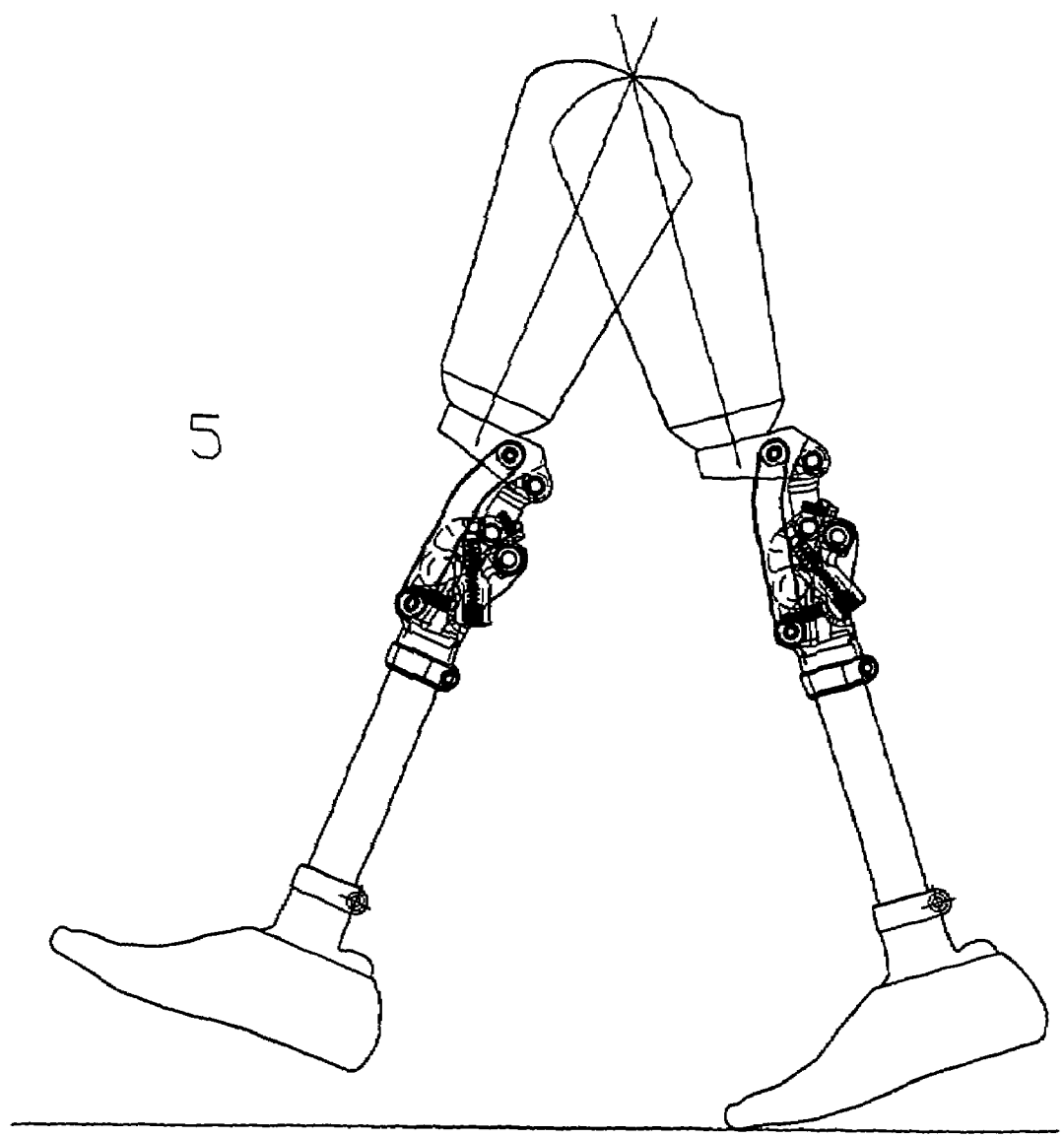
FIG. 7 is a schematic view showing the states of the knee joints of FIG. 1 when they are equipped on both prosthetic legs during walking.

FIG. 7 is a schematic view showing the states of the knee joints according to the present embodiment when they are equipped on both prosthetic legs during waking.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

I claim:

1. A knee joint for a prosthetic leg comprising an upper member for connecting to the thigh of said prosthetic leg, a lower member for connecting to the shin and foot of said prosthetic leg, a linking device for connecting the upper and lower members, a cushion element, and a resilient device, wherein said linking device comprises a joining element and a plurality of connecting rods;

said resilient device comprises a supporting element, a first cap element, a first helical spring, a first adjustment screw, a second cap element, a second helical spring, a second adjustment screw, and a stopping plate;

an upper portion of said joining element is hinged to fork arms of said upper member by a first axle, said first axle is fixedly locked by a first positioning screw on said joining element, a plurality of cushion blocks are configured on said joining element at where said joining element interfaces with said upper member, said joining element has an adjustment screw in the front;

an lower portion of said joining element is hinged to fork arms of said supporting element by a second axle, said second axle is fixedly locked by at least a second positioning screw on said supporting element, said supporting element has a tubular portion extended from the bottom of said supporting element for receiving said first cap element, said first helical spring, and said first adjustment screw inside, said first cap element, said first helical spring, and said first adjustment screw, along with said adjustment screw of said joining element, confines the angle between said joining element and said supporting element, said first adjustment screw controls the force exerted by said first helical spring;

a front protruding portion of said supporting element is hinged to fork arms of said lower member by a third axle, said third axle is fixedly locked by a third positioning screw on said supporting element;

needles bearings are installed in through holes of said upper and lower members, top ends of said connecting rods are bolted to a lateral through hole in the middle of said upper member by a plurality of screws, bottom ends of said connecting rods are bolted to a lateral through hole in the back of said lower member by a plurality of screws, a second cap element, a second helical spring, a second adjustment screw, and a stopping plate are installed inside a threaded hole on said lower member between said fork arms of said lower member, said second cap element is pressed against said tubular portion of said supporting element, said second adjustment screw controls the force exerted by said second helical spring; and said cushion element, made of a plastic material, is positioned on a curved seat in the back of said lower member and confined by said connecting rods, said cushion element absorbs the shock when said prosthetic leg is walking or standing.

* * * * *